United States Patent [19]

Robert

[11] 4,081,553
[45] Mar. 28, 1978

[54] CYTOPROTECTIVE PROSTAGLANDINS FOR USE IN HUMAN INTESTINAL DISEASES

[75] Inventor: André Robert, Kalamazoo, Mich.

[73] Assignee: The Upjohn Company, Kalamazoo, Mich.

[21] Appl. No.: 658,148

[22] Filed: Feb. 17, 1976

[51] Int. Cl.$^2$ ............... A61K 31/215; A61K 31/19
[52] U.S. Cl. .................................... 424/305; 424/317
[58] Field of Search .............................. 424/305, 317

[56] References Cited

U.S. PATENT DOCUMENTS

| | | | |
|---|---|---|---|
| 3,849,487 | 11/1974 | Bundy | 424/317 |
| 3,927,213 | 12/1975 | Lippmann | 424/317 |
| 3,928,588 | 12/1975 | Robert | 424/317 |

*Primary Examiner* — Sam Rosen
*Attorney, Agent, or Firm* — Robert A. Armitage

[57] ABSTRACT

The present invention provides a method for treatment of Crohn's disease, inflammatory bowel disease, infectious enteritis, sprue, and intestinal inflammatory disease secondary to radiation exposure or an intestinally-manifested allergic response to foodstuffs which comprises administrating a cytoprotective prostaglandin to a human who suffers from one of said diseases. Cytoprotective prostaglandins refer to those prostaglandin-type compounds which are useful in reducing the incidence of NOSAC-induced lesions in the intestinal wall of the rat. "NOSAC" is an abbreviation for "non-steroidal antiinflammatory compound."

4 Claims, No Drawings

CYTOPROTECTIVE PROSTAGLANDINS FOR USE IN HUMAN INTESTINAL DISEASES

BACKGROUND OF THE INVENTION

The present invention comprises the surprising and unexpected discovery that administration of a cytoprotective prostaglandin provides a useful method for treatment of certain diseases of the human small or large intestine.

Certain pharmacological uses of prostaglandins or prostaglandin analogs in the treatment or prophylaxis of gastrointestinal tract disorders are known in the art. For example, the use of prostaglandin-type compounds effective in reducing gastric secretion and in the cure or prophylaxis of gastric or duodenal ulcers is known. See U.S. Pat. Nos. 3,903,297 and 3,781,429. Further, the concomitant use of prostaglandin-type compounds with a NOSAC (nonsteroidal antiinflammatory compound which is a prostaglandin synthetase inhibitor) is known to be effective to reduce known undesirable gastrointestinal side effects of NOSAC administration. See U.S. Pat. Nos. 3,911,124; 3,917,828; 3,928,588; and 3,927,213.

Finally, the use of $PGE_2$ to prevent damage to the gastric mucosal barrier in the dog when the gastric mucosal barrier is subjected to attack by aspirin or indomethacin is described in Gastroenterology 68:A-19/876 (April, 1975).

As used herein, the term prostaglandin refers to those cyclopentane-containing carboxylic acids derived from mammalian tissues which are structural derivatives of prostanoic acid:

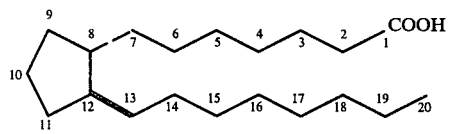

See Bergstrom, et al. Pharmacol. Rev. 20, 1 (1968) and references cited therein. For example, prostaglandin $E_2$ ($PGE_2$) exhibits the following structure:

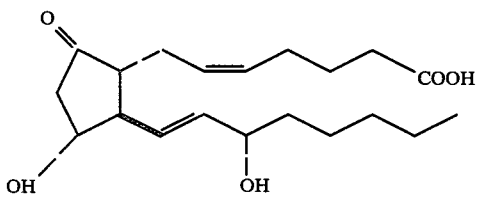

The term prostaglandin analog herein refers to those compounds structurally related to the prostaglandins (in that they exhibit a cyclopentane, or adjacently homologous cycloalkane, ring and a pair of side chains attached to adjacent carbon atoms of the ring) which retain characteristic biological properties of the prostaglandins. See Bergstrom, cited above. Various structural modifications of the prostaglandins are known to produce useful prostaglandin analogs. For example, the replacement of the carboxy with a hydroxymethyl is known, substitution of a methyl, ethyl, or fluoro for a hydrogen at, for example, C-2 or C-16, and replacement of a methylene by an oxa or thia at, for example, C-5 is known. Further, partially deoxygenated prostaglandins are known to be useful prostaglandin analogs. Accordingly, 9-deoxy, 11-deoxy, and 15-deoxy-prostaglandins are known. Finally, there are known prostaglandin analogs wherein the double bonds of, for example, $PGF_{2\alpha}$ are shifted, e.g., cis-4,5-didehydro-$PGF_{1\alpha}$, or replaced by triple bonds, e.g., 13,14-didehydro-$PGF_{2\alpha}$.

As used herein, the term prostaglandin-type compound refers to any prostaglandin or prostaglandin-analog.

The small and large intestine of all mammalian species are subject to a wide variety of diseases. The present invention is concerned with six such diseases: Crohn's disease, inflammatory bowel disease, tropical and nontropical sprue, infectious enteritis, and intestinal inflammatory disease secondary to radiation exposure or ingestion of certain foodstuffs (e.g., dairy products, wheat gluten, or certain seafoods to which susceptible humans exhibit an intestinally-manifested allergic response). These diseases are readily diagnosed by conventional and readily-ascertainable means to those of ordinary skill in the art. For example, see Kirschner, et al., Ed., Inflammatory Bowel Disease, Lea and Febiger, 1975.

Causes of intestinal inflammatory diseases secondary to radiation exposure include those derived from x-ray, $\gamma$-ray, cosmic radiation, and alpha or beta radiation (particularly when emitted from ingested radioactive materials) exposure. Additionally, intestinal inflammatory disease secondary to radiation exposure is caused by a wide variety of particulate radiation, e.g., subatomic particles ($\pi$-mesons) and anti-matter particles (positrons), in addition to the sources described above. Accordingly, this inflammatory disease can result from radiation therapy when, for example, employed in the treatment of cancer.

Finally, the prostaglandin-type compounds are known to be useful pharmacological agents capable of conventional formulations and administration by a wide variety of routes. See U.S. Pat. Nos. 3,903,297 for a description of typical methods of formulation and administration.

SUMMARY OF THE INVENTION

The present invention provides a method for treating Crohn's disease, inflammatory bowel disease, infectious enteritis, sprue, intestinal inflammatory disease secondary to ingestion of certain foodstuffs to which susceptible humans exhibit an intestinally manifested allergic response, or intestinal inflammatory disease secondary to radiation exposure, which comprises:

administering to a human who is suffering from one of said diseases an amount of a cytoprotective prostaglandin effective to cure said disease.

In accomplishing the purposes of this invention those compounds which are useful as cytoprotective prostaglandins are those prostaglandins or prostaglandin analogs which are at least one-tenth (0.1) as potent as $PGE_2$ in effecting a 50 percent reduction in intestinal lesions in indomethacin-treated rats according to the method of A. Robert, Gastroenterology 69:1045 (1975). In accomplishing the purposes of the present invention, however, it is particularly preferred to employ those cytoprotective prostaglandins which are at least as potent as, and more preferably more potent than, $PGE_2$ in exhibiting intestinal lesion inhibiting properties, as described above.

With regard to this invention any convenient route of administration is employed. Thus, oral formulation and oral administration is, for example, the preferred route although other routes, such as via a naso-gastric tube or suppositories and enemas are employed. See U.S. Pat. No. 3,903,297 for a description of various formulations and routes of administration encompassed in the present invention.

The dosage regimen for the cytoprotective prostaglandin in accord with this invention will depend upon a variety of factors, including the type, age, weight, sex, and medical condition of the mammal, the nature and severity of the disease, and the particular cytoprotective prostaglandin to be administered. It is within the skill of the attending physician or veterinarian to determine the presence of one of the above diseases and to prescribe an effective amount of the cytoprotective prostaglandin to reduce and then substantially to eliminate the symptoms of the disease. In doing that, the physician or veterinarian would by one method start at a relatively low dose of the cytoprotective prostaglandin, for example, about 0.25 mg./kg./day to about 0.1 $\mu$g./kg./day, and observe the response of the human or animal patient for a few days. The dose of the cytoprotective prostaglandin is then adjusted downward or upward until the minimum effective dose is found. For example, the maximum needed dose is usually between about 25 mg./kg./day and about 15 $\mu$g./kg./day, although it may be necessary occasionally to exceed these doses when the disease is especially severe. Once the minimum effective dose of the particular cytoprotective prostaglandin is determined for a particular subject, it is advantageous to provide the subject with a dosage schedule which will provide a substantially uniform level of cytoprotective prostaglandin in the intestinal wall.

I claim:

1. A method of treatment of Crohn's disease, inflammatory bowel disease, sprue, or intestinal inflammatory disease secondary to an intestinally manifested allergic response to foodstuffs, which comprises:

administering to a human who suffers from said disease an amount of cytoprotective prostaglandin effective to cure said disease.

2. A method according to claim 1, wherein said disease is Crohn's disease.

3. A method according to claim 1, wherein said disease is inflammatory bowel disease.

4. A method according to claim 1, wherein said disease is sprue.

* * * * *